US010765876B2

(12) United States Patent
Nikolski

(10) Patent No.: US 10,765,876 B2
(45) Date of Patent: Sep. 8, 2020

(54) METHOD AND APPARATUS FOR DELIVERING ANTI-TACHYCARDIA PACING

(71) Applicant: Medtronic, Inc., Minneapolis, MN (US)

(72) Inventor: Vladimir P. Nikolski, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 196 days.

(21) Appl. No.: 15/964,261

(22) Filed: Apr. 27, 2018

(65) Prior Publication Data

US 2019/0329061 A1   Oct. 31, 2019

(51) Int. Cl.
*A61N 1/39* (2006.01)
*A61B 5/04* (2006.01)
*A61B 5/0456* (2006.01)
*A61B 5/0464* (2006.01)
*A61N 1/365* (2006.01)

(52) U.S. Cl.
CPC ........ *A61N 1/3987* (2013.01); *A61B 5/04011* (2013.01); *A61B 5/0456* (2013.01); *A61B 5/0464* (2013.01); *A61N 1/3925* (2013.01); *A61N 1/3956* (2013.01); *A61B 5/04017* (2013.01); *A61N 1/36585* (2013.01)

(58) Field of Classification Search
CPC .. A61N 1/3987; A61N 1/3956; A61N 1/3925; A61B 5/0464; A61B 5/0456
USPC .......................................................... 607/5
See application file for complete search history.

(56) References Cited

U.S. PATENT DOCUMENTS

| 5,148,812 A | 9/1992 | Verrier et al. |
| 5,458,619 A | 10/1995 | Olson |
| 5,792,065 A | 8/1998 | Xue et al. |
| 5,861,009 A | 1/1999 | Armstrong et al. |
| 6,957,105 B2 | 10/2005 | Pastore et al. |
| 7,027,867 B2 | 4/2006 | Park et al. |
| 7,225,014 B1 | 5/2007 | Province |

(Continued)

FOREIGN PATENT DOCUMENTS

| WO | 2007095612 A2 | 8/2007 |
| WO | 2016126613 A1 | 8/2016 |

(Continued)

OTHER PUBLICATIONS (PCT/US2019/026871) PCT Notification of Transmittal of the International Search Report and the Written Opinion of the International Searching Authority, dated Jul. 11, 2019, 13 pages.

*Primary Examiner* — Amanda K Hulbert
*Assistant Examiner* — Philip C Edwards

(57) ABSTRACT

A medical device is configured to deliver anti-tachycardia pacing (ATP) in the presence of T-wave alternans. The device is configured to detect a ventricular tachyarrhythmia from a cardiac electrical signal received by the medical device. In response to the detected ventricular tachyarrhythmia, the device delivers a plurality of ATP pulses at alternating time intervals. The alternating time intervals comprise at least a first ATP time interval separating a first pair of the ATP pulses and a second ATP time interval different than the first ATP time interval. The second ATP time interval consecutively follows the first ATP time interval and separates a second pair of the ATP pulses.

23 Claims, 9 Drawing Sheets

(56) References Cited

U.S. PATENT DOCUMENTS

| | | |
|---|---|---|
| 7,245,968 B1 | 7/2007 | Farazi et al. |
| 7,257,443 B2 | 8/2007 | Pastore et al. |
| 7,689,279 B2 | 3/2010 | Ziegler et al. |
| 7,725,172 B2 | 5/2010 | Rouw et al. |
| 7,761,150 B2 | 7/2010 | Ghanem et al. |
| 7,881,789 B2 | 2/2011 | Pastore et al. |
| 7,894,899 B2 | 2/2011 | Sharma |
| 7,933,650 B2 | 4/2011 | Li |
| 8,255,043 B2 | 8/2012 | Qu et al. |
| 8,634,903 B2 | 1/2014 | Sharma et al. |
| 8,676,306 B2 | 3/2014 | Qu et al. |
| 8,855,763 B2 | 10/2014 | Li |
| 8,874,198 B2 | 10/2014 | Qu et al. |
| 8,886,296 B2 | 11/2014 | Patel |
| 8,914,106 B2 | 12/2014 | Charlton et al. |
| 8,942,795 B2 | 1/2015 | Gunderson et al. |
| 9,597,525 B2 | 3/2017 | Cao et al. |
| 9,795,789 B2 | 10/2017 | Kaiser |
| 9,855,414 B2 | 1/2018 | Marshall et al. |
| 2004/0167579 A1* | 8/2004 | Sharma ................ A61N 1/3621 607/14 |
| 2004/0220631 A1 | 11/2004 | Burnes et al. |
| 2006/0116592 A1 | 6/2006 | Zhou et al. |
| 2006/0116596 A1 | 6/2006 | Zhou |
| 2007/0191894 A1 | 8/2007 | Li |
| 2010/0004713 A1* | 1/2010 | Warren ............... A61B 5/04525 607/17 |
| 2011/0245700 A1 | 10/2011 | Ghanem et al. |
| 2012/0316613 A1 | 12/2012 | Keefe et al. |
| 2015/0306375 A1 | 10/2015 | Marshall et al. |
| 2016/0114168 A1 | 4/2016 | Demmer et al. |
| 2016/0158567 A1 | 6/2016 | Marshall et al. |
| 2018/0028828 A1 | 2/2018 | Cao et al. |

FOREIGN PATENT DOCUMENTS

| | | |
|---|---|---|
| WO | 2017160507 A1 | 9/2017 |
| WO | 2017189484 A1 | 11/2017 |

\* cited by examiner

METHOD AND APPARATUS FOR DELIVERING ANTI-TACHYCARDIA PACING

TECHNICAL FIELD

This disclosure relates to a medical device and method for delivering anti-tachycardia pacing (ATP) in the presence of T-wave alternans (TWA).

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical electrical leads may be configured to position electrodes or other sensors at desired locations for delivery of electrical stimulation or sensing of physiological conditions. For example, electrodes or sensors may be carried along a distal portion of a lead that is extended subcutaneously, submuscularly, or transvenously. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical pulses to the heart to address abnormal cardiac rhythms.

IMDs capable of delivering electrical pulses for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, a pacemaker or ICD may deliver pacing pulses to the heart upon detecting bradycardia or tachycardia. An ICD may deliver high voltage cardioversion or defibrillation shocks to the heart upon detecting fast ventricular tachycardia or fibrillation.

SUMMARY

The techniques of this disclosure generally relate to a medical device and method for delivering anti-tachycardia pacing (ATP) in the presence of T-wave alternans (TWA). The ATP pulses are separated by alternating ATP time intervals corresponding to alternating phases of a Q-T or R-T time interval present during TWA. In some examples, the TWA may be detected before and/or after the onset of the ATP pulses for establishing the alternating ATP time intervals. In other examples, sensing of T-waves during ATP delivery enables ATP pulses to be delivered after sensed T-waves resulting in alternating ATP time interval in the presence of TWA.

In one example, the disclosure provides a medical device including a sensing circuit, a therapy delivery circuit and a control circuit. The sensing circuit is configured to receive a cardiac electrical signal from a patient's heart and sense R-waves and T-waves from the cardiac electrical signal. The therapy delivery circuit is configured to generate and deliver ATP pulses to the patient's heart via electrodes coupled to the therapy delivery circuit. The control circuit is coupled to the sensing circuit and to the therapy delivery circuit and is configured to detect a ventricular tachyarrhythmia from the cardiac electrical signal received by the sensing circuit. Responsive to the detected ventricular tachyarrhythmia, the control circuit controls the therapy delivery circuit to deliver a series of ATP pulses including alternating ATP time intervals separating the ATP pulses. The alternating ATP time intervals include at least a first ATP time interval separating a first pair of the ATP pulses and a second ATP time interval separating a second pair of the ATP pulses. The second ATP time interval is different than the first ATP time interval and consecutively follows the first ATP time interval.

In another example, the disclosure provides a method that includes detecting a ventricular tachyarrhythmia from a cardiac electrical signal device of a patient's heart and responsive to detecting the ventricular tachyarrhythmia, delivering a plurality of ATP pulses including alternating time intervals separating the ATP pulses in the series. The alternating time intervals include at least a first ATP time interval separating a first pair of the ATP pulses and a second ATP time interval separating a second pair of the ATP pulses. The second ATP time interval is different than the first ATP time interval and consecutively follows the first ATP time interval.

In yet another example, the disclosure provides a non-transitory computer-readable medium storing a set of instructions which when executed by a control circuit of a medical device, cause the medical device to detect a ventricular tachyarrhythmia from a cardiac electrical signal received by the medical device and, responsive to the detected ventricular tachyarrhythmia, control a therapy delivery circuit of the medical device to deliver a series of ATP pulses including alternating ATP time intervals separating the ATP pulses in the series. The alternating time intervals include at least a first ATP time interval separating a first pair of the ATP pulses and a second ATP time interval separating a second pair of the ATP pulses. The second ATP time interval is different than the first ATP time interval and consecutively follows the first ATP time interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for delivering ATP in the presence of TWA. The T-wave in a cardiac electrical signal, e.g., a surface electrocardiogram, intrathoracic electrogram or intracardiac electrogram signal, is the signal attendant to the repolarization of the ventricular myocardium. TWA is the beat-to-beat variation of the amplitude, shape and/or timing of the T-wave. TWA may therefore represent the temporal and spatial dispersion of repolarization of the myocardium. TWA may be present during a tachyarrhythmia and may be altered or introduced during delivery of ATP to treat the tachyarrhythmia.

The timing of ATP pulses may be important in successfully terminating ventricular tachycardia (VT). In order to increase the likelihood of terminating VT, each ATP pulse is delivered during a time interval that the myocardium is likely to be in a non-refractory, excitable state between tachyarrhythmia depolarization wavefronts. This time interval is referred to as the "excitable gap." During the excitable gap, an ATP pulse that captures the myocardial tissue evokes a myocardial depolarization that collides with a propagating tachycardia depolarization wavefront and blocks the re-entrant circuit of the tachycardia thereby resetting the re-entrant circuit or terminating the VT. The timing and duration of the excitable gap may change beat-by-beat due to TWA, which may potentially reduce the effectiveness of ATP pulses delivered at a fixed inter-pulse interval. Techniques for delivering ATP are presented herein for accounting for changes in the excitable gap timing and duration due to TWA to increase the likelihood of successfully terminating VT even in the presence of TWA.

Figure 1A:
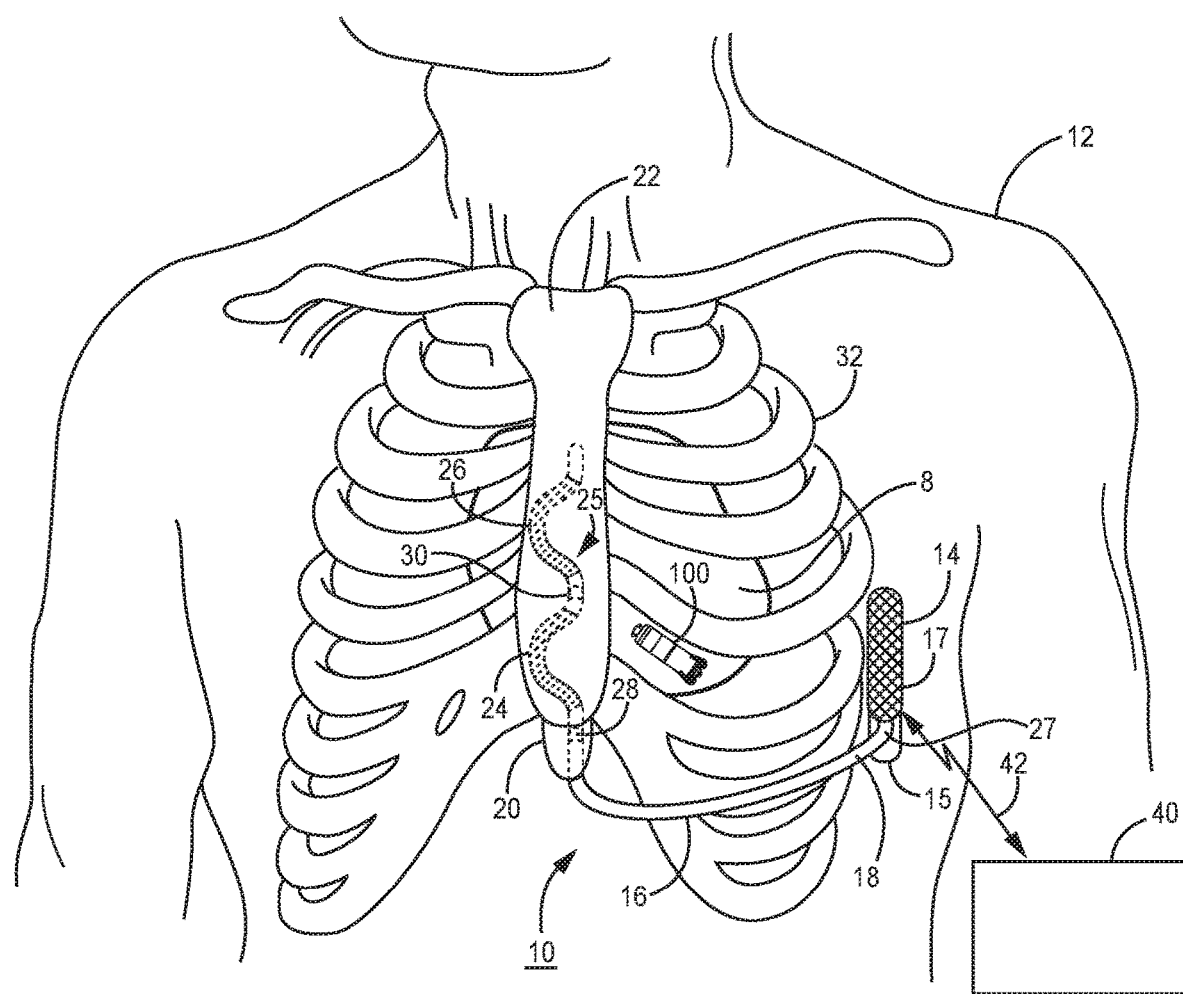
FIGS. 1A and 1B are conceptual diagrams of an extra-cardiovascular ICD system capable of delivering ATP according to one example.
Figure 1B:
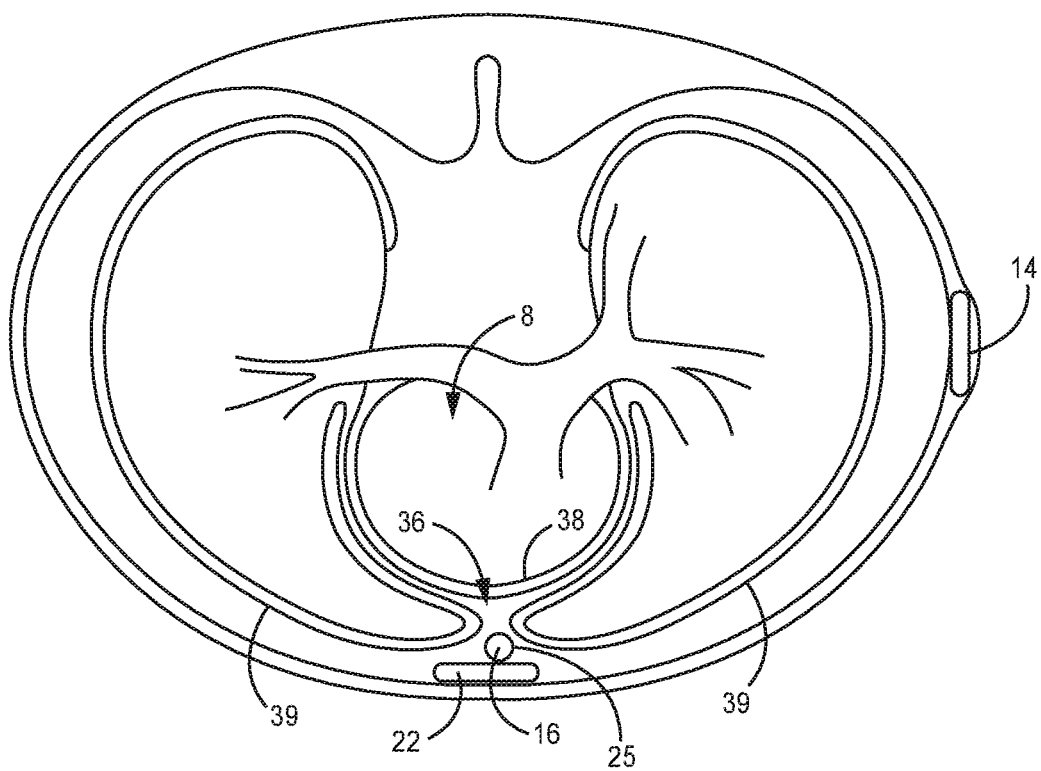

FIGS. 1A and 1B are conceptual diagrams of an extra-cardiovascular ICD system 10 according to one example. FIG. 1A is a front view of ICD system 10 implanted within patient 12. FIG. 1B is a transverse sectional view of ICD system 10 implanted within patient 12. ICD system 10 includes an ICD 14 connected to an extra-cardiovascular electrical stimulation and sensing lead 16. An "extra-cardiovascular" lead as used referred to herein, refers to a lead that is implanted outside the heart and blood vessels of the patient's cardiovascular system. An extra-cardiovascular lead may extend subcutaneously, sub-muscularly or intra-thoracically, for example. FIGS. 1A and 1B are described in the context of an ICD system 10 capable of providing defibrillation/cardioversion (CV/DF) shocks and pacing pulses, including ATP pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses in conjunction with lead-based cathode electrodes. In other instances, the housing 15 of ICD 14 may include a plurality of electrodes on an outer portion of the housing. The outer portion(s) of the housing 15 functioning as an electrode(s) may be coated with a material, such as titanium nitride to reduce post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, electrical sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28 and 30. In some cases, defibrillation electrodes 24 and 26 may be configured to be activated concurrently. Alternatively or additionally, each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage CV/DF shock therapy applications. Electrodes 24 and 26 may be used in a pacing electrode vector for delivering extra-cardiovascular pacing pulses such as ATP pulses and/or in a sensing vector used to sense cardiac electrical signals and detect ventricular tachycardia (VT) and ventricular fibrillation (VF).

Electrodes 28 and 30 are relatively smaller surface area electrodes for delivering relatively lower voltage pacing pulses and for sensing cardiac electrical signals. Electrodes 28 and 30 are referred to herein as pace/sense electrodes because they are generally configured for use in low voltage applications, e.g., used as either a cathode or anode for delivery of pacing pulses, which may include ATP pulses, and/or sensing of cardiac electrical signals. In some instances, electrodes 28 and 30 may provide only pacing functionality, only sensing functionality or both.

In the example illustrated in FIG. 1A, electrode 28 is located proximal to defibrillation electrode 24, and electrode 30 is located between defibrillation electrodes 24 and 26. In other examples, electrodes 28 and 30 may be positioned at other locations along lead 16, which may include one or more pace/sense electrodes. Electrodes 28 and 30 are illustrated as ring electrodes, however electrodes 28 and 30 may comprise any of a number of different types of electrodes, including ring electrodes, short coil electrodes, hemispherical electrodes, directional electrodes, or the like.

Lead 16 extends subcutaneously or submuscularly over the ribcage 32 medially from the connector assembly 17 of ICD 14 toward a center of the torso of patient 12, e.g., toward xiphoid process 20 of patient 12. At a location near xiphoid process 20, lead 16 bends or turns and extends superiorly within anterior mediastinum 36 in a substernal position. Anterior mediastinum 36 (seen in FIG. 1B) may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 1A and 1B, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8. Other implant locations and lead and electrode arrangements that may be used in conjunction with the ATP techniques described herein are generally disclosed in U.S. Publication No. 2015/0306375 (Marshall, et al.) and U.S. Pat. No. 9,855,414 (Marshall, et al.), both of which are incorporated herein by reference in their entirety. For example, lead 16 may extend superiorly and subcutaneously or submuscularly over the ribcage and/or sternum 22, rather than substernally. Alternatively, lead 16 may be placed along other subcutaneous or submuscular paths. The path of lead 16 may depend on the location of ICD 14, the arrangement and position of electrodes carried by the lead distal portion 25, and/or other factors.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

Electrical conductors (not illustrated) extend through one or more lumens of the elongated lead body 18 of lead 16 from the lead proximal end 27 to electrodes 24, 26, 28, and 30 located along the distal portion 25 of the lead body 18. The conductors electrically couple respective ones of the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

ICD 14 may obtain electrical signals corresponding to electrical activity of heart 8 via a combination of sensing vectors that include combinations of electrodes 28 and 30. In some examples, housing 15 of ICD 14 is used in combination with one or more of electrodes 28 and/or 30 in a sensing electrode vector. ICD 14 may even obtain cardiac electrical signals using a sensing vector that includes one or both defibrillation electrodes 24 and/or 26, e.g., between electrodes 24 and 26 or between one of electrodes 24 or 26 in combination with one of electrodes 28, 30 and/or housing 15.

ICD 14 analyzes the cardiac electrical signals received from one or more of the sensing vectors to monitor for abnormal rhythms, such as bradycardia, VT and VF. ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30 and/or housing 15. The pacing electrode vector may be different than the sensing electrode vector. In one example, cardiac electrical signals are sensed between pace/sense electrodes 28 and 30, and ATP pulses are delivered between pace/sense electrode 30 used as a cathode electrode and defibrillation electrode 24 used as a return anode electrode. In other examples, ATP pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and ATP electrode vectors may be selected according to individual patient need.

The myocardial site that is first captured by an ATP pulse delivered by the selected extra-cardiovascular pacing electrode vector is referred to herein as the "capture site" which is spaced apart from the pacing cathode electrode and the pacing anode electrode that are not in direct contact with the myocardium in an extra-cardiovascular ICD system, such as system 10. In order to successfully terminate a detected VT, it is desirable that all ATP pulses capture the myocardium to overdrive pace the heart back into a normal sinus rhythm. In order to overdrive pace the heart, each pacing pulse of the ATP sequence should arrive at the capture site during the excitable gap and before the next expected intrinsic ventricular depolarization. During TWA, the onset and duration of the excitable gap may vary beat to beat. TWA may be present at the time of a VT detection and may persist during ATP delivery, with or without being altered. In other instances, TWA may not be present at the time of VT detection but may arise during ATP delivery. As described below, ICD 14 is configured to deliver ATP pulses at time intervals that take into account beat-to-beat variations in the timing of the excitable gap due to TWA.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and the housing 15 of ICD 14.

FIGS. 1A and 1B are illustrative in nature and should not be considered limiting of the practice of the techniques disclosed herein. For instance, ICD 14 is shown implanted subcutaneously on the left side of patient 12 along the ribcage 32. ICD 14 may, in other instances, be implanted between the left posterior axillary line and the left anterior axillary line of patient 12. ICD 14 may be implanted at other subcutaneous or submuscular locations in patient 12 such as in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well and include other electrode and lead body configurations.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver ATP according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

In some examples, ICD 14 may be co-implanted with an intracardiac pacemaker 100. For example, when lead 16 is implanted subcutaneously, pacing pulses of an ATP therapy may require amplitudes that are uncomfortable or painful for a patient. Intracardiac pacemaker 100 may be a leadless device implantable wholly within a heart chamber, e.g., within the right ventricle or left ventricle, for delivering electrical stimulation pulses, including ATP, via electrodes coupled to the housing of pacemaker 100. Pacemaker 100 may be capable of delivering ATP therapy, either in response to detecting VT or VF or in response to receiving a communication signal from ICD 14.

Figure 2:
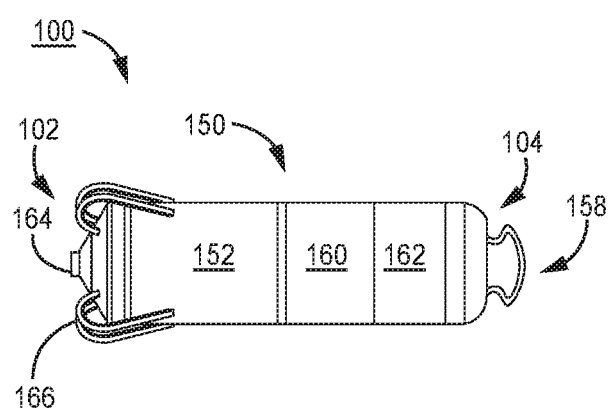
FIG. 2 is a conceptual diagram of a pacemaker that may be configured to perform the ATP techniques disclosed herein.

As shown in FIG. 2, pacemaker 100 includes electrodes 162 and 164 spaced apart along its housing 150 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 100 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, polyether ether ketone (PEEK), or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 100 as attributed to an IMD performing the ATP delivery techniques described herein. Housing 150 further includes a battery subassembly 160, which provides power to the control electronics subassembly 152.

Pacemaker 100 may include a set of fixation tines 166 to secure pacemaker 100 to patient tissue, e.g., by actively engaging with the ventricular endocardium and/or interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position.

Pacemaker 100 may optionally include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber, such as the right or left ventricle.

In some examples, pacemaker 100 may be a triggered pacemaker that delivers a pacing pulse in response to a trigger signal transmitted by ICD 14. Pacemaker 100 may receive a command from ICD 14 to initiate ATP therapy and deliver the ATP pulses according to timing interval data received from ICD 14. In other examples, pacemaker 100 may analyze cardiac signals received via electrodes 162 and 164 for determining when a pacing pulse is needed, including detecting VT or VF and delivering an ATP therapy. As such, pacemaker 100 may be configured to detect TWA and adjust ATP pulse timing according to the techniques disclosed herein.

Figure 3:
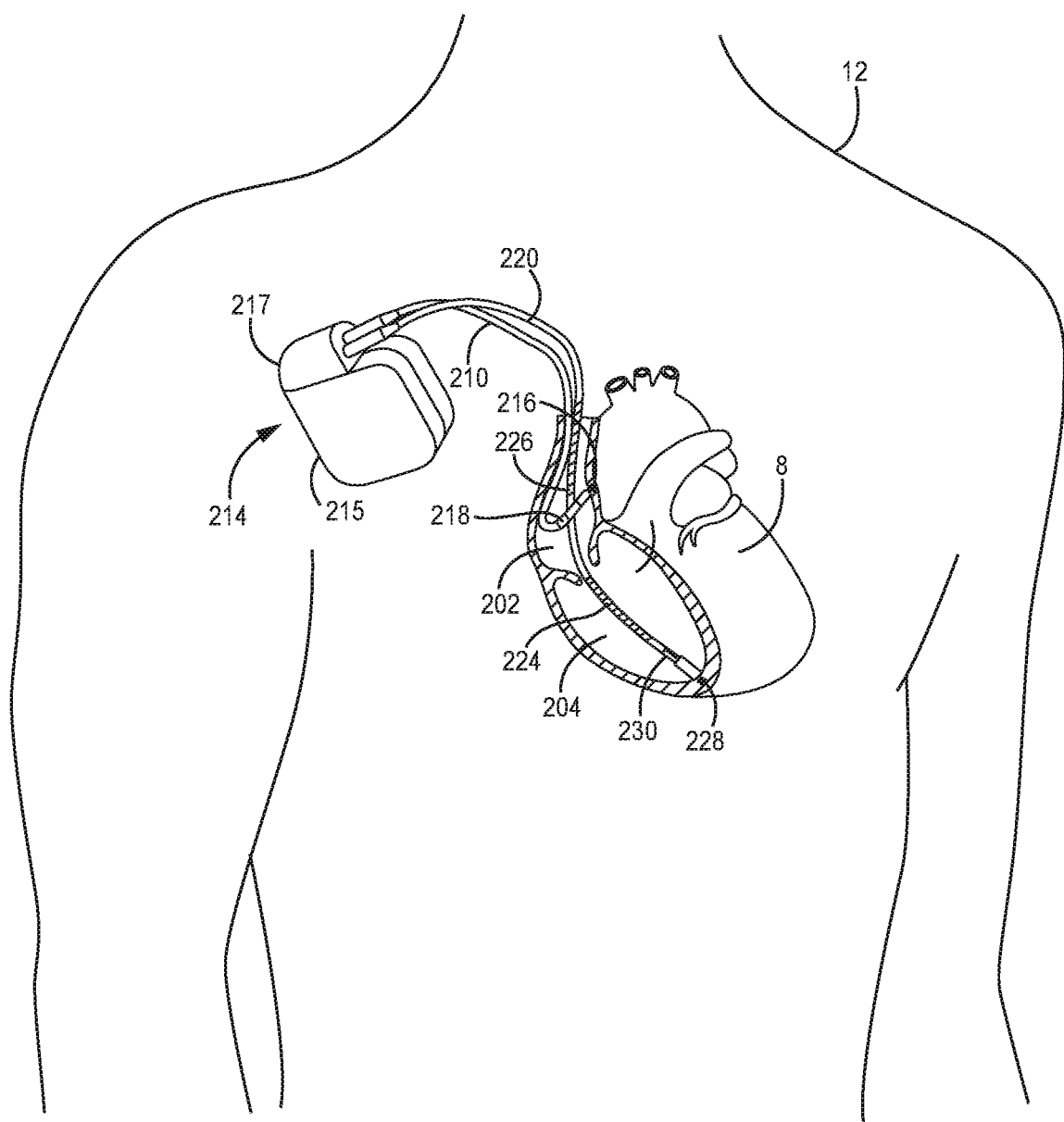
FIG. 3 is a conceptual diagram of a patient implanted with an ICD according to another example.

FIG. 3 is a conceptual diagram of patient 12 implanted with an ICD 214 according to another example. In this example, ICD 214 is coupled to one or more transvenous leads carrying electrodes for sensing cardiac electrical signals and for delivering electrical stimulation therapy, e.g., bradycardia pacing, ATP, cardiac resynchronization therapy (CRT) and/or CV/DF. ICD 214 is shown implanted in a right pectoral position in FIG. 3; however it is recognized that ICD 214 may be implanted in a left pectoral position, particularly when ICD 214 includes sensing, pacing, cardioversion and/or defibrillation capabilities using housing 215 as an electrode.

ICD 214 is illustrated as a dual chamber device for sensing and therapy delivery in an atrial chamber 202 and a ventricular chamber 204 of heart 8. As such, ICD 214 includes connector assembly 217 having two connector bores for receiving proximal connectors of a right atrial (RA) lead 210 and a right ventricular (RV) lead 220. In other examples ICD 214 may be a single chamber device, e.g., connectable only to RV lead 220, or a multi-chamber device including a third connector bore, e.g., for receiving a coronary sinus lead to enable ICD 214 to sense left ventricular signals and deliver electrical stimulation pulses to the LV.

RA lead 210 may carry a distal tip electrode 216 and ring electrode 218 spaced proximal from the tip electrode 216 for delivering pacing pulses to the right atrium 202 and obtaining atrial electrical signals for producing an atrial intracardiac electrogram (EGM) signal by ICD 214. RV lead 220 may carry pacing and sensing electrodes 228 and 230 for delivering RV pacing pulses to the right ventricle 204 and obtaining ventricular electrical signals for producing an RV EGM signal by ICD 214. RV lead 220 may also carry RV defibrillation electrode 224 and a superior vena cava (SVC) defibrillation electrode 226. Defibrillation electrodes 224 and 226 are shown as coil electrodes spaced apart proximally from the distal pacing and sensing electrodes 228 and 230.

ICD housing 215 encloses circuitry, as further described below, configured to detect arrhythmias and provide electrical stimulation therapy, such as bradycardia pacing, post-shock pacing, ATP, CRT and/or CV/DF shock therapy, using the electrodes 216, 218, 224, 226, 228 and 230 of transvenous leads 210 and 220. As described below, ICD 214 may adjust the time of ATP pulse delivery pulse-by-pulse based on detecting TWA and identifying the phase of the TWA.

Figure 4:
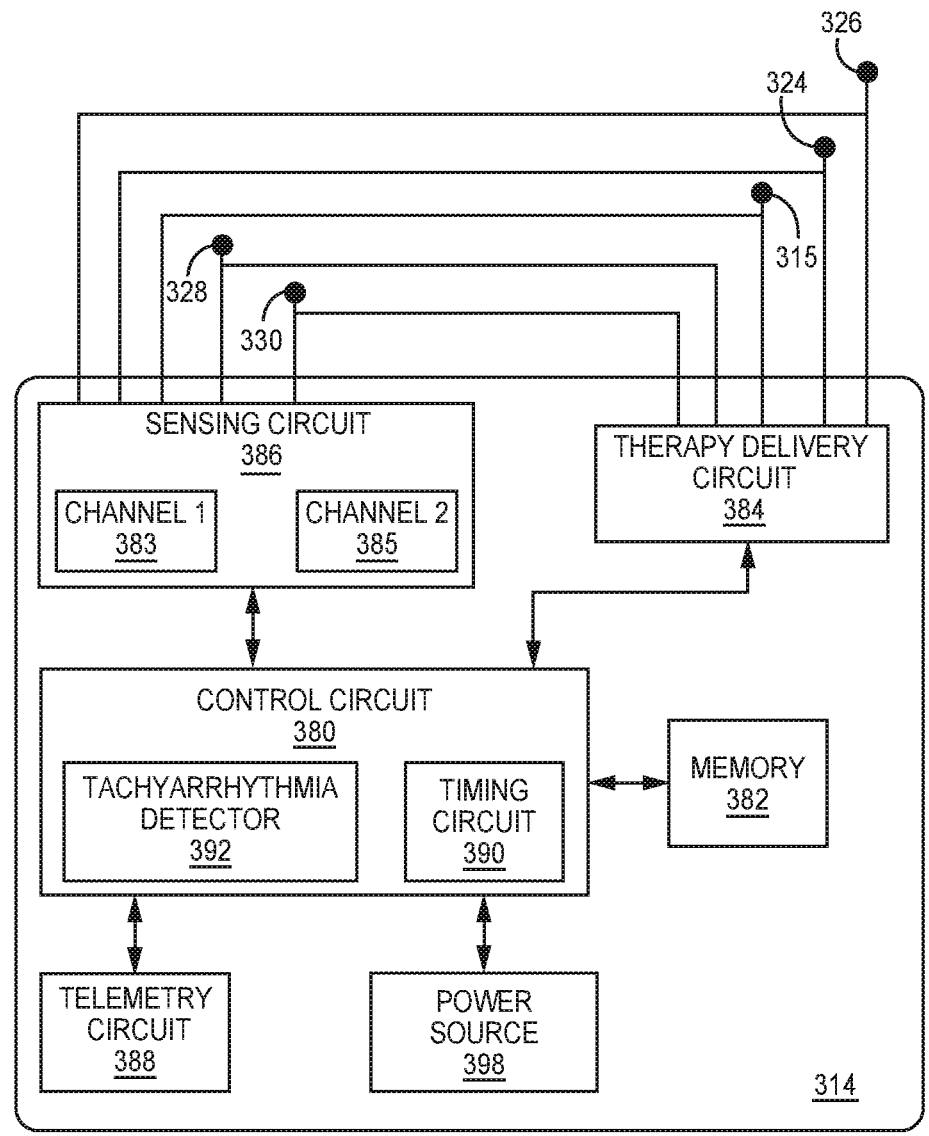
FIG. 4 is a schematic diagram of an ICD according to one example.

FIG. 4 is a schematic diagram of ICD 314 according to one example. The electronic circuitry enclosed within housing 315 (shown schematically as an electrode in FIG. 4) includes software, firmware and hardware that cooperatively monitor one or more cardiac electrical signals, determine when an electrical stimulation therapy is necessary, and deliver therapies as needed according to programmed therapy delivery algorithms and control parameters. The software, firmware and hardware are configured to detect VT and VF for determining when ATP or CV/DF shocks are required. ICD 314 shown schematically in FIG. 4 may generally correspond to ICD 14 shown in FIGS. 1A and 1B coupled to an extra-cardiovascular lead (such as lead 16 carrying extra-cardiovascular electrodes 24, 26, 28, and 30) or to ICD 214 shown in FIG. 3 coupled to at least one transvenous lead (e.g., lead 220 carrying defibrillation electrodes 224 and 226 and pace/sense electrodes 228 and 230). Functions attributed to the circuitry described in conjunction with FIG. 4 may be adapted as needed for detecting VT and VF and delivering ATP via extra-cardiovascular electrodes or via endocardial electrodes. Furthermore, it is contemplated that the functionality for delivering ATP pulses adjusted to account for changes in the timing of the excitable gap due to TWA may be implemented in an intracardiac pacemaker, e.g., pacemaker 100 shown in FIG. 2, which may include all or a portion of the example components illustrated in FIG. 4.

ICD 314 includes a control circuit 380, memory 382, therapy delivery circuit 384, sensing circuit 386, and telemetry circuit 388. A power source 398 provides power to the circuitry of ICD 314, including each of the components 380, 382, 384, 386, and 388 as needed. Power source 398 may include one or more energy storage devices, such as one or more rechargeable or non-rechargeable batteries. The connections between power source 398 and each of the other components 380, 382, 384, 386 and 388 are to be understood from the general block diagram of FIG. 3, but are not shown for the sake of clarity. For example, power source 398 may be coupled to one or more charging circuits included in therapy delivery circuit 384 for charging holding capacitors included in therapy delivery circuit 384 that are discharged at appropriate times under the control of control circuit 380 for producing electrical pulses according to a therapy protocol, such as for bradycardia pacing, CRT, post-shock pacing, ATP and/or CV/DF shock pulses. Power source 398 may also be coupled to components of sensing circuit 386, such as sense amplifiers, analog-to-digital converters, switching circuitry, etc., telemetry circuit 388, and memory 382 to provide power as needed.

The functional blocks shown in FIG. 4 represent functionality included in an ICD configured to sense cardiac electrical signals and deliver cardiac electrical stimulation therapy and may include any discrete and/or integrated electronic circuit components that implement analog and/or digital circuits capable of producing the functions attributed to an ICD (or pacemaker) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern IMD system, given the disclosure herein, is within the abilities of one of skill in the art.

Control circuit 380 communicates, e.g., via a data bus, with therapy delivery circuit 384 and sensing circuit 386. Therapy delivery circuit 384 and sensing circuit 386 are electrically coupled to electrodes 324, 326, 328, 330 and the housing 315, which may function as a common or ground electrode or as an active can electrode for delivering CV/DF shock pulses or cardiac pacing pulses. Sensing circuit 386 may be selectively coupled to electrodes 328, 330 and/or housing 315 in order to monitor electrical activity of the patient's heart. Sensing circuit 386 may additionally be selectively coupled to defibrillation electrodes 324 and/or 326 for use in a sensing electrode vector together or in combination with one or more of electrodes 328, 330 and/or housing 315. Sensing circuit 386 may be enabled to selectively receive cardiac electrical signals from at least two sensing electrode vectors from the available electrodes 324, 326, 328, 330, and housing 315. For example, sensing circuit 386 may include switching circuitry (not shown) for selecting which of electrodes 324, 326, 328, 330, and housing 315 are coupled to a first sensing channel 383 and which are coupled to a second sensing channel 385 of sensing circuit 386. Switching circuitry may include a switch array, switch matrix, multiplexer, or any other type of switching device suitable to selectively couple components of sensing circuit 386 to selected electrodes. In other instances, ICD 314 may include only a single sensing channel.

In the case of two sensing channels, two cardiac electrical signals from two different sensing electrode vectors may be received simultaneously by sensing circuit 386. The two sensing electrode vectors may include two different ventricular sensing electrode vectors each coupled to a respective sensing channel 383 and 385. In other examples, when an atrial sensing electrode vector is available, e.g., when RA lead 210 is present carrying atrial pacing and sensing electrodes 216 and 218 (as shown in FIG. 3), one sensing channel 383 may be an atrial sensing channel and one sensing channel 385 may be a ventricular sensing channel.

Sensing circuit 386 may monitor one or both or the cardiac electrical signals for sensing cardiac electrical events, e.g., P-waves attendant to the depolarization of the atrial myocardium, R-waves attendant to the depolarization of the ventricular myocardium, and T-waves attendant to myocardial repolarization in the ventricles. Sensing circuit 386 may produce digitized cardiac signal waveforms for analysis by control circuit 380 for detecting a cardiac rhythm, including detection of TWA.

In some examples, one sensing channel, e.g., channel 383, may be configured to sense R-waves from a cardiac electrical signal obtained using a first sensing electrode vector selected from the available electrodes 324, 326, 328, 330 and housing 315. The second sensing channel 385 may be configured to sense T-waves from the same cardiac electrical signal or a different cardiac electrical signal obtained using a second sensing electrode vector different than the first vector. In some examples, T-wave sensing includes rejecting R-waves based on the timing of R-waves sensed by the first sensing channel.

Each sensing channel 383 and 385 may be configured to amplify, filter and digitize the cardiac electrical signal received from selected electrodes coupled to the respective sensing channel to improve the signal quality for detecting cardiac electrical events, such as R-waves and T-waves or performing other signal analysis. The cardiac event detection circuitry within sensing circuit 386 may include one or more sense amplifiers, filters, rectifiers, threshold detectors, comparators, analog-to-digital converters (ADCs), timers or other analog or digital components. A cardiac event sensing threshold may be automatically adjusted by sensing circuit 386 under the control of control circuit 380, based on timing intervals and sensing threshold values determined by control circuit 380, stored in memory 382, and/or controlled by hardware, firmware and/or software of control circuit 380 and/or sensing circuit 386. For instance, an R-wave sensing threshold and a T-wave sensing threshold may each be stored in memory 382 and applied by sensing circuit 386 as auto-adjusting thresholds that include one or more decay rates and/or step adjustments. When the cardiac electrical signal crosses the respective sensing threshold, a cardiac event is sensed. For example, when the cardiac electrical signal crosses a R-wave sensing threshold an R-wave is sensed. As another example, when the cardiac electrical signal crosses a T-wave sensing threshold and is not concurrent with a sensed R-wave, the sensing circuit may sense a T-wave. These T-waves may be used in detecting TWA by control circuit 380 as described further herein.

Upon sensing a cardiac electrical signal (e.g., an R-wave, T-wave or P-wave) based on a sensing threshold crossing, sensing circuit 386 may produce a sensed event signal, such as an R-wave sensed event signal, T-wave sensed event signal or P-wave sensed event signal, which is passed to control circuit 380. The R-wave sensed event signals may be used by control circuit 380 for determining ventricular event intervals, referred to herein as "RR intervals" or "RRIs" for detecting tachyarrhythmia and determining a need for therapy. A ventricular event interval or RRI is the time interval between two consecutively sensed R-waves and may be determined between two consecutive R-wave sensed event signals received from sensing circuit 386. For example, control circuit 380 may include a timing circuit 390 for determining RRIs between consecutive R-wave sensed event signals received from sensing circuit 386 and for controlling various timers and/or counters used to control the timing of therapy delivery by therapy delivery circuit 384, including the timing of ATP pulses as described herein. Timing circuit 390 may additionally set time windows such as morphology template windows, morphology analysis windows or perform other timing related functions of ICD 314 including synchronizing CV/DF shocks or other therapies delivered by therapy delivery circuit 384 with sensed cardiac events.

T-wave sensed event signals may be passed from sensing circuit 386 to control circuit 380 for use in detecting and characterizing TWA. In some examples, timing circuit 390 may receive R-wave sensed event signals and T-wave sensed event signals from sensing circuit 386 for determining R-T intervals. TWA may be detected by control circuit 380 in response to beat-to-beat variation in R-T intervals. An R-T interval is the time interval between a sensed R-wave and a subsequently sensed T-wave of the cardiac cycle determined using sensed event signals received from sensing circuit 386. The phase of the TWA may be determined based on the R-T intervals. For example, the R-T intervals may alternate between a first phase, which may be a relatively longer R-T interval, and a second phase, which may be a relatively shorter R-T interval. Detection of TWA and identification of the phase, e.g., short or long phase based on R-T interval, may be used by control circuit 380 in controlling the timing of ATP pulses delivered by therapy delivery circuit 384.

Tachyarrhythmia detector 392 is configured to analyze signals received from sensing circuit 386 for detecting tachyarrhythmia episodes. Tachyarrhythmia detector 392 may be implemented in control circuit 380 as software, hardware and/or firmware that processes and analyzes signals received from sensing circuit 386 for detecting VT and/or VF. In some examples, tachyarrhythmia detector 392 may include comparators and counters for counting RRIs determined by timing circuit 390 that fall into various rate detection zones for determining a ventricular rate or performing other rate- or interval-based assessments for detecting and discriminating VT and VF. For example, tachyarrhythmia detector 392 may compare the RRIs determined by timing circuit 390 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 392.

When a VT or VF interval counter reaches a threshold count value, referred to as "number of intervals to detect" or "NID," a ventricular tachyarrhythmia may be detected by control circuit 380. Tachyarrhythmia detector 392 may be configured to perform other signal analysis for determining if other detection criteria are satisfied before detecting VT or VF when an NID is reached. For example, cardiac signal analysis may be performed to determine if R-wave morphology criteria, onset criteria, and noise and oversensing rejection criteria are satisfied in order to determine if the VT/VF detection should be made or withheld.

To support additional cardiac signal analyses performed by tachyarrhythmia detector 392, sensing circuit 386 may pass a digitized cardiac electrical signal to control circuit 380. A cardiac electrical signal from the selected sensing channel, e.g., from first sensing channel 383 and/or the second sensing channel 385, may be passed through a filter and amplifier, provided to a multiplexer and thereafter converted to multi-bit digital signals by an analog-to-digital converter, all included in sensing circuit 386, for storage in memory 382. Additional signal analyses may include morphological analysis of pre-determined time segments of the cardiac electrical signals or QRS waveforms. In some examples, additional analysis may be performed to detect TWA based on changes in the T-wave of a ventricular electrical signal, such as changes in T-wave amplitude, polarity, Q-T interval, R-T interval or the like. Detection of TWA performed by control circuit 380 may occur before and/or during ATP delivery in some examples.

Therapy delivery circuit 384 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 384 according to control signals received from control circuit 380. Timing circuit 390 of control circuit 380 includes various timers or counters that control when ATP or other cardiac pacing pulses are delivered. For example, timing circuit 390 may include programmable digital counters set by a microprocessor of the control circuit 380 for controlling the basic pacing time intervals associated with various pacing modes or ATP sequences delivered by ICD 314. The microprocessor of control circuit 380 may also set the amplitude, pulse width, polarity or other characteristics of the cardiac pacing pulses, which may be based on programmed values stored in memory 382.

In response to detecting VT or VF, control circuit 380 may control therapy delivery circuit 384 to deliver therapies such as ATP and/or CV/DF therapy. Therapy can be delivered by initiating charging of high voltage capacitors via a charging circuit, both included in therapy delivery circuit 384. Charging is controlled by control circuit 380, which monitors the voltage on the high voltage capacitors passed to control circuit 380 via a charging control line. When the voltage reaches a predetermined value set by control circuit 380, a logic signal is generated on a capacitor full line and passed to therapy delivery circuit 384, terminating charging. A CV/DF pulse is delivered to the heart under the control of the timing circuit 390 by an output circuit of therapy delivery circuit 384 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. In some examples, the high voltage therapy circuit configured to deliver CV/DF shock pulses can be controlled by control circuit 380 to deliver pacing pulses, e.g., for delivering ATP or post shock pacing pulses. In other examples, therapy delivery circuit 384 may include a low voltage therapy circuit for generating and delivering relatively lower voltage pacing pulses for a variety of pacing needs, including ATP.

Control parameters utilized by control circuit 380 for detecting cardiac arrhythmias and controlling therapy delivery may be programmed into memory 382 via telemetry circuit 388. Telemetry circuit 388 may include a transceiver and antenna for communicating with external device 40 (shown in FIG. 1A) using RF communication as described above. Under the control of control circuit 380, telemetry circuit 388 may receive downlink telemetry from and send uplink telemetry to external device 40. Telemetry circuit 388 may be used to transmit and receive communication signals to/from another medical device implanted in patient 12, such as pacemaker 100.

Figure 5:
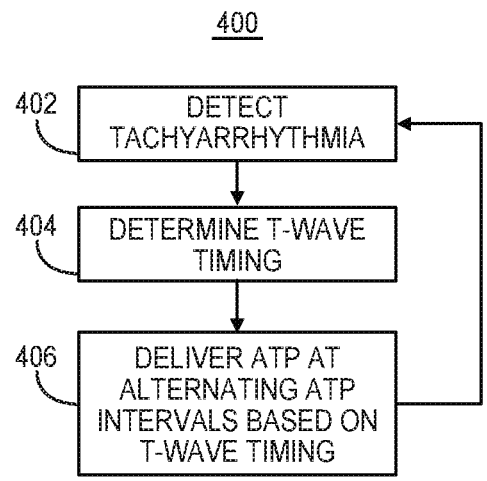
FIG. 5 is a flow chart of a method for delivering ATP according to one example.

FIG. 5 is a flow chart 400 of a method for delivering ATP according to one example. FIG. 5 and other flow charts (e.g., FIGS. 6-8) presented herein are described in conjunction with the circuitry of ICD 314 of FIG. 4. As indicated above, ICD 314 may correspond to ICD 14 of FIGS. 1A and 1B coupled to an extra-cardiovascular lead or to ICD 214 of FIG. 3, coupled to one or more transvenous leads. It is to be understood, however, that the ATP delivery techniques described in conjunction with the flow charts presented herein are not limited for use by an ICD. A pacemaker, such as intracardiac pacemaker 100 of FIG. 2, may be capable of delivering ATP therapy and may be configured to control the timing of ATP pulses in the presence of TWA using the techniques disclosed herein. In other examples, any device capable delivering ATP may be adapted to perform the techniques disclosed herein, including external pacemakers and defibrillators.

At block 402, control circuit 380 detects a ventricular tachyarrhythmia for which ICD 314 is programmed to deliver ATP. ATP may be programmed as a therapy delivered in response to detecting VT but may also be programmed as a therapy delivered in response to detecting VF since ATP is sometimes delivered during high voltage capacitor charging in an attempt to avert the need for CV/DF shock delivery. The ventricular tachyarrhythmia may be detected according to a detection protocol implemented in ICD 314. Practice of the techniques for controlling ATP delivery as presented herein is not limited to use with a particular tachyarrhythmia detection protocol.

At block 404, control circuit 380 determines the timing of T-waves sensed by sensing circuit 386. The timing of T-waves sensed by the sensing circuit 386 is used by control circuit 380 for controlling the therapy delivery circuit 384 to deliver ATP at block 406. Therapy delivery circuit 384 is configured to deliver the ATP pulses at alternating ATP time intervals that are controlled based on the T-wave timing determined at block 404. As will be described in greater detail below, the T-wave timing may be determined at block 404 prior to ATP delivery. The T-wave timing determined prior to ATP delivery may be used to detect TWA and used to establish at least two alternating ATP intervals that separate consecutive ATP pulses. The alternating ATP intervals provide for delivery of each ATP pulse early during the excitable gap following each T-wave when TWA persists during ATP delivery.

In other examples, the T-wave timing may be determined at block 404 contemporaneously with ATP delivery. A T-wave may be sensed by sensing circuit 386 after each of at least two consecutive ATP pulses. Two different ATP time intervals may be established based on two different times determined from each delivered pulse to a subsequent T-wave. The two ATP time intervals may be used for delivering the ATP pulses at alternating ATP time intervals corresponding to the alternating timing of T-waves during TWA persisting or arising during ATP delivery. In still other examples, a combination of determining T-wave timing preceding ATP delivery and determining T-wave timing during ATP delivery may be performed at block 404 in order to control the therapy delivery circuit 384 to deliver ATP pulses at alternating ATP time intervals at block 406, based on T-wave timing in the presence of TWA.

Based on the T-wave timing, control circuit 380 controls therapy delivery circuit 384 to deliver a series of ATP pulses at alternating time intervals. The alternating time intervals may include at least a first ATP time interval separating an earliest occurring pair of the ATP pulses and a second ATP time interval different than the first ATP time interval and consecutively following the first ATP time interval. The second ATP time interval separates a second pair of the ATP pulses consecutively following the earliest occurring pair. For example, a first ATP time interval may separate the first and second ATP pulses of a series of ATP pulses, and a second ATP time interval different than the first may separate the second and third ATP pulses of the series of ATP pulses. The first and second ATP intervals may continue to alternate between consecutively delivered ATP pulses of the series until the programmed number of ATP pulses in the series has been delivered. In another example, the alternating ATP time intervals may be ceased upon no longer detecting TWA.

Depending on the phase of the TWA during the cardiac cycle in which ATP is initiated, the first ATP time interval may be longer or shorter than the second ATP time interval. In some examples, as described below, TWA may be detected prior to delivering ATP. The R-T interval of each phase of the TWA may be determined. In this case, the phase of the TWA (e.g., a short R-T interval phase or a long R-T interval phase) on the cycle that the first ATP pulse is being delivered may be determined by control circuit 380. Additionally or alternatively, the phase of the TWA may be determined on a cycle preceding the cycle during which the first ATP pulse is to be delivered so that the TWA phase of the cardiac cycle during which the first ATP pulse is delivered can be predicted with relatively high confidence. The first ATP interval following the first, leading ATP pulse may be set based on the expected phase and R-T interval of the detected TWA. In other examples, previous determination of the phase and R-T intervals of TWA is not required. TWA may not be present or may not be detected prior to ATP delivery. In these cases, sensing of T-waves during ATP delivery may be used by control circuit 380 to control the timing of ATP pulses at alternating ATP time intervals corresponding to alternating phases of TWA that are present during ATP delivery.

The alternating ATP time intervals may be short-long-short-long, etc., until the series of ATP pulses is complete. In other instances, the alternating ATP time intervals may be long-short-long-short, etc., until the series of ATP pulses is complete, depending on the TWA phase of the first cycle following the first ATP pulse. Furthermore, it is to be understood that the alternating ATP time intervals may generally follow a short-long-short-long or long-short-long-short alternating pattern that does not necessarily require each short ATP time interval to be equal to each other short ATP time interval or each long ATP time interval be equal to each other long ATP time interval. Some variation in the T-wave timing during each short and long phase of the TWA may occur. T-wave sensing during ATP delivery may enable control circuit 380 to make adjustments to the timing of an ATP pulse cycle-by-cycle based on T-wave sensing during ATP delivery. As long as TWA is present, however, these cycle-by-cycle adjustments may still produce alternating cycles of relatively shorter and relatively longer ATP intervals.

After delivering ATP, control circuit 380 may return to block 402 to re-detect the tachyarrhythmia, if not successfully terminated by the ATP, or detect the next tachyarrhythmia episode. If the tachyarrhythmia is not successfully terminated, another ATP attempt may be performed according to a programmed menu of therapies. One or more additional attempts at terminating the tachyarrhythmia using ATP, which may include alternating ATP time intervals, may be made after the first ATP therapy. Adjustments to the subsequent ATP therapy attempts may be made. In some cases, if a maximum number of attempts of ATP therapies fail to terminate the tachyarrhythmia, a cardioversion/defibrillation shock is delivered.

Figure 6:
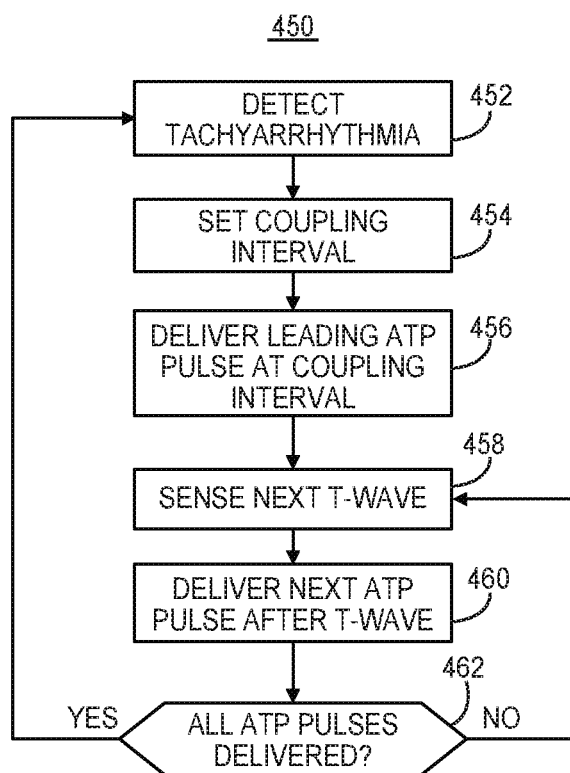
FIG. 6 is a flow chart of a method for controlling ATP pulses by a medical device according to another example.

FIG. 6 is a flow chart 450 of a method for controlling ATP pulses by a medical device according to another example. At block 452, control circuit 380 of ICD 314 detects a ventricular tachyarrhythmia. At block 454, control circuit 380 may set a coupling interval by determining a cycle length of the detected tachyarrhythmia (e.g., a median, minimum or most recent RR interval of the detected tachyarrhythmia). The coupling interval may be a time interval set to a percentage or pre-determined interval less than the tachyarrhythmia cycle length. The first, leading ATP pulse of a series of ATP pulses may be delivered at block 456 at the coupling interval following an R-wave sensed by sensing circuit 386.

In another example, control circuit 380 may set the coupling interval at block 454 based on the timing of a T-wave sensed prior to the first ATP pulse. Sensing circuit 382 may pass an R-wave sensed event signal to control circuit 380 followed by an immediately consecutive T-wave sensed event signal passed to control circuit 380. Control circuit 380 may deliver the first, leading ATP pulse at block 456 consecutive with the sensed T-wave, at a coupling interval set based on the timing of the immediately preceding T-wave. As such, the coupling interval may be set as a fixed time interval following the sensed T-wave.

After delivering the first, leading ATP pulse, sensing circuit 386 is configured to sense a T-wave following the first ATP pulse at block 458. At block 460, control circuit 380 delivers the next ATP pulse after the sensed T-wave such that the second ATP pulse is delivered following the first ATP pulse at a first ATP interval based on the timing of the T-wave sensed after the first ATP pulse. If all ATP pulses of the programmed ATP therapy have not been delivered, as determined at block 462, sensing circuit 386 senses the next T-wave, consecutively following the second ATP pulse, at block 458 and controls the therapy delivery circuit 384 to deliver the third ATP pulse at block 460 at a second ATP interval, consecutively following the first ATP interval, and separating the second and third ATP pulses. The second ATP interval will either be longer or shorter than the first ATP interval depending on the phase of TWA that has either arisen or persisted during the delivery of the ATP pulses.

This process of sensing a T-wave consecutively following each ATP pulse and delivering an ATP pulse at a fixed interval after each sensed T-wave continues until all ATP pulses of the series of ATP pulses have been delivered. In the presence of TWA, the ATP intervals separating consecutively delivered ATP pulses alternate between relatively longer and relatively shorter ATP intervals based on the timing of the sensed T-waves. Detection of TWA prior to ATP delivery is not required to establish the alternating ATP intervals. The ATP pulses may be delivered at a fixed interval after sensing a T-wave. Since the T-waves occur at alternating R-T intervals in the presence of TWA, the resulting ATP time intervals between consecutive ATP pulses will alternate between relatively longer and shorter ATP time intervals.

Figure 7:
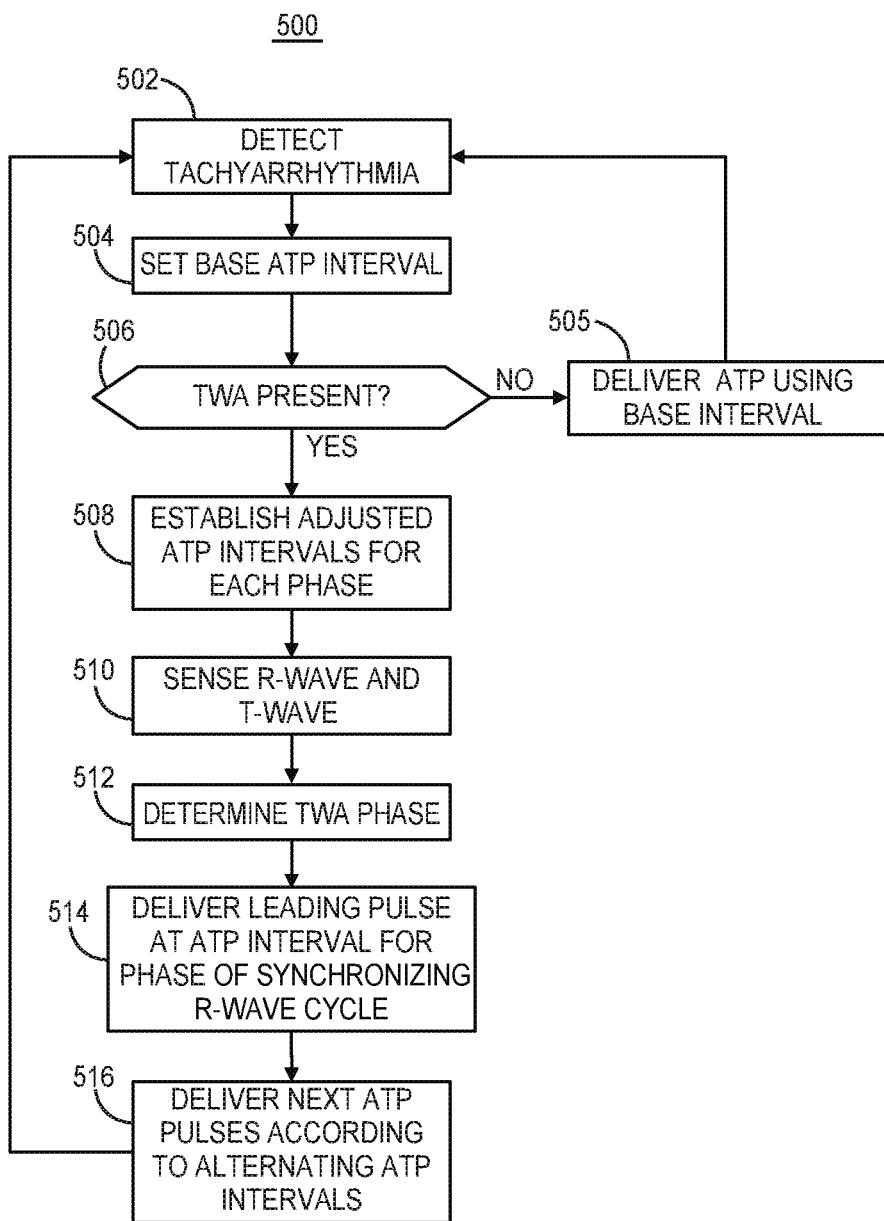
FIG. 7 is a flow chart of a method for controlling ATP delivery after detecting TWA according to another example.

FIG. 7 is a flow chart 500 of a method for controlling ATP delivery after detecting TWA according to another example. At block 502, control circuit 380 detects a ventricular tachyarrhythmia episode for which ATP therapy is programmed to be delivered. At block 504, control circuit 380 may set a base ATP interval by determining the cycle length of the detected VT or VF. The base ATP interval may be a fixed interval or percentage less than the determined cycle length. The base ATP interval may be the ATP interval used for delivering ATP pulses in the absence of TWA.

At block 506, control circuit 380 may analyze the cardiac electrical signal(s) received from sensing circuit 386 for detecting TWA. Control circuit 380 may determine R-T intervals between consecutive R-wave sensed event signals and T-wave sensed event signals received from sensing circuit 386. If the differences between consecutive R-T intervals are greater than a threshold difference and represent alternating R-T intervals, TWA may be detected. Various TWA detection criteria may be applied to the cardiac electrical signal(s) received from sensing circuit 386. The techniques used for detecting the presence of TWA prior to delivering ATP are not limited to any particular TWA detection technique. The techniques for detecting TWA, however, generally include detection of beat-to-beat variation of the R-T or Q-T time interval, or more generally the relative timing of the T-wave in the cardiac cycle, indicating that the onset of the excitable gap and its duration may be varying from beat-to-beat.

If TWA is not present, ATP may be delivered at block 505 using the base ATP interval determined at block 504. After a leading ATP pulse is delivered at a coupling interval, which may or may not be equal to the base ATP interval, each ATP pulse may be delivered at the base ATP interval following a preceding ATP pulse, at progressively shorter (decrementing) intervals starting from the base ATP interval (e.g., a ramp ATP therapy) or other ATP protocol based on the base ATP interval that does not include alternating ATP time intervals to account for TWA.

In response to detecting TWA at block 506, control circuit 380 may establish adjusted ATP time intervals at block 508 for delivering ATP in the presence of TWA. The R-T time interval for each short and long phase of the TWA may be determined at block 508. The R-T time interval may be determined for each phase by averaging or determining a median, mode, minimum, maximum range or other characterization of multiple, alternating short R-T intervals and of multiple alternating long R-T intervals. In some examples, TWA detection may occur simultaneously with tachyarrhythmia detection such that setting a base ATP interval at block 504 is not required. Instead, two different ATP time intervals may be established at block 508 in response to detecting TWA simultaneously with detecting the tachyarrhythmia.

At block 510, control circuit 380 receives an R-wave sensed event signal followed by a T-wave sensed event signal from sensing circuit 386. Control circuit 380 determines if the current cardiac cycle including the sensed R-wave and T-wave (block 510) is the short or long phase of the TWA at block 512. Based on this determination of the TWA phase, the leading pulse of the ATP therapy may be delivered at block 514 at one of the two established ATP time intervals following the next R-wave sensed event signal. For instance, if the current R-T time interval is the short phase of the TWA, the next cardiac cycle is expected to have a relatively longer R-T time interval. The leading ATP pulse may be synchronized to the next sensed R-wave (the "synchronizing" R-wave) by delivering the leading ATP pulse after the next sensed R-wave following the longer one of the two ATP intervals established at block 508. If the R-T interval determined at block 512 is the long phase of the TWA, the leading pulse of the ATP sequence may be scheduled after the shorter ATP time interval following the next sensed, synchronizing R-wave.

Subsequent ATP pulses are delivered at block 516 according to the established alternating ATP time intervals to provide correspondence with the alternating short and long phases of the TWA detected prior to the onset of ATP. The two different ATP time intervals are established to enable delivery of the ATP pulses as early as possible during the excitable gap without being delivered into the T-wave during either phase. After ATP delivery, control circuit 380 may return to block 502 to continue monitoring the heart rhythm and delivering additional therapies as needed and in accordance with a programmed sequence of tachyarrhythmia therapies.

In a variation of the method shown in FIG. 7, the leading ATP pulse may be delivered at block 514 at a coupling interval determined by control circuit 380 based on the cycle length of the detected ventricular tachyarrhythmia. The second ATP pulse may be delivered following the leading ATP pulse at an ATP time interval set to one of the two established ATP intervals, either short or long, based on the expected phase of the TWA for the cycle beginning with the second ATP pulse. The expected phase of the TWA is known from determining the TWA phase of a cardiac cycle preceding the leading ATP pulse.

To illustrate, the leading ATP pulse may be delivered following a synchronizing R-wave at a coupling interval that is set based on the tachyarrhythmia cycle length. The coupling interval may be different than both of the ATP time intervals established at block 508 based on the alternating phases of the detected TWA. An R-T interval immediately preceding the leading ATP pulse may be determined to correspond to the short phase of the TWA. In this example, the leading ATP pulse starts an expected long phase of the TWA since it was immediately preceded by the short phase. As such, the second ATP pulse may be delivered at the long ATP interval following the leading ATP pulse to correspond to the expected long phase of the TWA. The second ATP pulse marks the start of an expected short phase of the TWA. The third ATP pulse is delivered at the short ATP interval established at block 508 to correspond to the short phase of the TWA. The third ATP pulse is separated from the second ATP pulse by the shorter one of the established ATP time intervals to coincide with the predicted short phase of the TWA that was detected prior to the start of ATP delivery. Subsequent ATP pulses are delivered at alternating short and long ATP time intervals to correspond to the phase of the TWA as predicted based on the TWA phase determined immediately prior to the leading ATP pulse.

Figure 8:
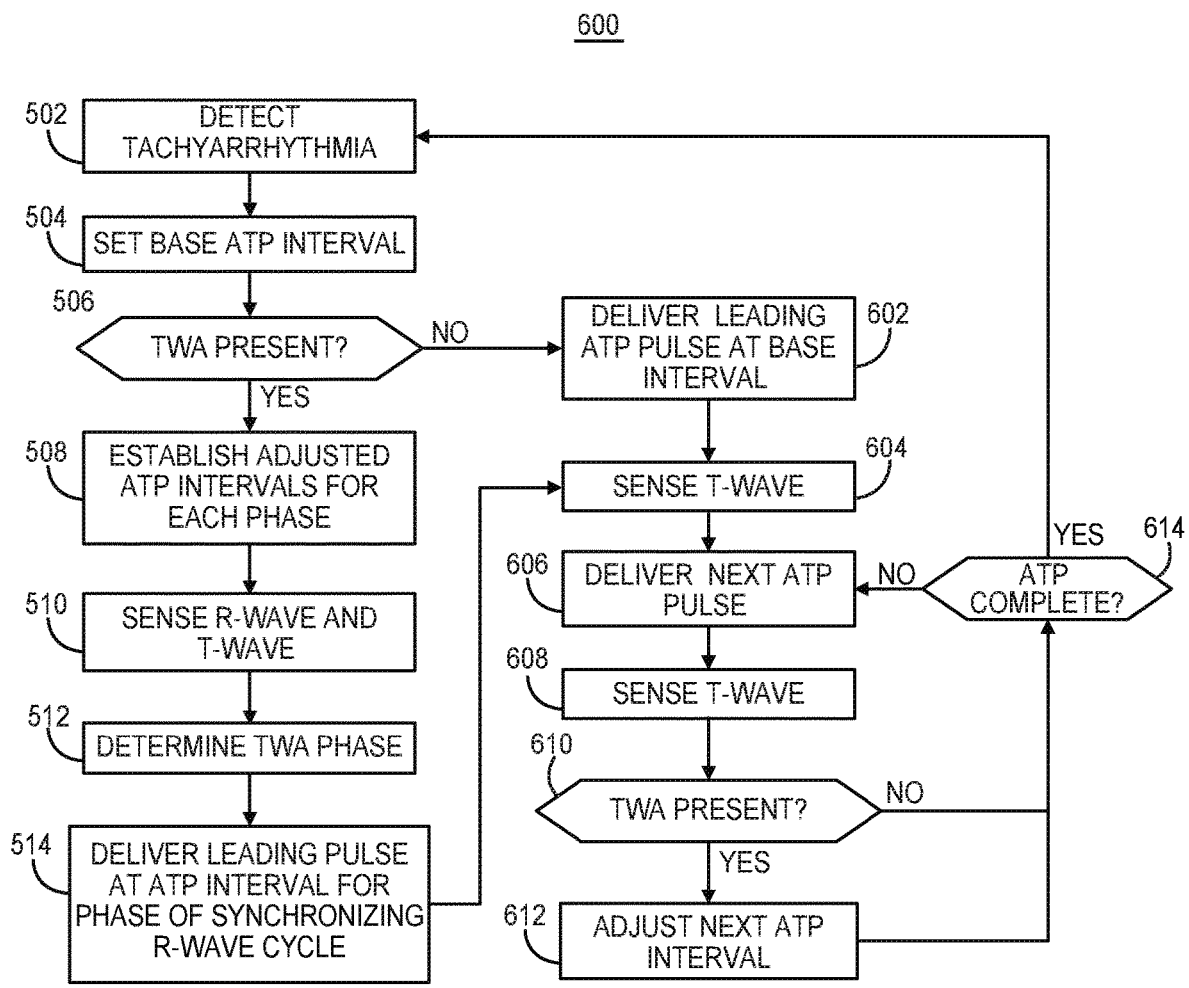
FIG. 8 is a flow chart of a method for controlling ATP pulses in the presence of TWA according to yet another example.

FIG. 8 is a flow chart 600 of a method for controlling ATP pulses in the presence of TWA according to another example. Blocks 502 through 514 correspond to identically numbered blocks described above in conjunction with FIG. 7. However instead of only applying ATP intervals established based on the R-T intervals and TWA phase detected before initiating ATP, ICD 314 may continue monitoring for TWA during ATP delivery to adjust ATP intervals on a cycle by cycle basis as needed. If TWA is detected prior to starting ATP ("yes" branch of block 506), the ATP intervals for each phase of the TWA may be established at block 508 by control circuit 380. The TWA phase of a cycle prior to the first, leading ATP pulse may be determined at block 512 based on determining an R-T interval. At block 514, control circuit 380 delivers the leading ATP pulse synchronized to a sensed R-wave at a selected coupling interval, which may be the ATP interval established for the phase of the cardiac cycle beginning with the synchronizing R-wave. In some cases, the leading ATP pulse may be delivered at the shorter ATP interval established at block 508 to increase TWA instability, which may help to terminate the tachyarrhythmia. In other cases, the leading ATP pulse may be delivered at the longer ATP interval established at block 508 to promote cardiac capture by the leading ATP pulse. In other examples, a coupling interval different than one of the two established ATP intervals may be used to synchronize the leading ATP pulse to the sensed R-wave at block 514. The coupling interval may be set based on the tachyarrhythmia cycle length to promote cardiac capture by the leading ATP pulse.

If TWA is not detected prior to initiating ATP ("no" branch of block 506), the leading ATP pulse may be synchronized to the sensed R-wave at block 602 at the ATP interval set at block 504 based on the tachyarrhythmia cycle length. The leading pulse may be delivered at the base ATP interval or a coupling interval, which may be shorter than the base ATP interval, following a sensed R-wave.

After the leading ATP pulse delivered at either block 514 or at block 502, sensing circuit 386 senses the T-wave following the leading ATP pulse at block 604 and determines the time interval between the leading ATP pulse and the sensed T-wave. At block 606, control circuit 380 controls therapy delivery circuit 384 to deliver the next ATP pulse at a selected ATP interval following the leading ATP pulse. If TWA was detected prior to the leading ATP pulse, the selected ATP interval may be one of the adjusted ATP intervals established at block 508 and selected according to the expected TWA phase for the current cycle. If TWA was not detected prior to the leading ATP pulse, the selected ATP interval for controlling the second ATP pulse delivery is the base ATP interval established at block 504.

After delivering the second ATP pulse, the subsequent T-wave is sensed by sensing circuit 386. Control circuit 380 determines the pulse to T-wave time interval from the second ATP pulse to the sensed T-wave. At block 610, control circuit 380 determines if TWA is present (or changed) based on the two T-wave time intervals determined at block 604 and 608. If TWA is not detected based on the two T-wave time intervals determined after the onset of ATP, e.g., following the leading ATP pulse and second ATP pulse, the next, third ATP pulse may be delivered at block 606 at the base ATP interval established at block 504 according to the tachyarrhythmia cycle length. In some instances, even if TWA was present prior to the leading ATP pulse, the TWA may not be present after ATP is initiated. In this case, the base ATP interval set according to the tachyarrhythmia cycle length may be used for completing the ATP therapy.

If TWA is detected at block 610 during ATP delivery but was not detected prior to the leading ATP pulse, the base ATP interval determined at block 504 may be adjusted at block 612 according to the T-wave time intervals determined at blocks 604 and 608 and the expected phase of the TWA. In some examples, the next ATP pulse may be delivered at an ATP interval that is adjusted from the previously established base ATP interval. In other examples, the next ATP pulse may already be scheduled at the base ATP interval such that the adjustment to the ATP time interval based on TWA detected at block 610, after ATP is started, is delayed for one ATP pulse interval. The second ATP pulse after detecting TWA may be delivered according to the expected TWA phase and the ATP interval adjustment made at block 612.

In other instances, TWA detected prior to the leading ATP pulse may still be present and relatively unchanged during ATP delivery. In this case, no additional adjustment to the next ATP interval is required at block 612. The adjusted ATP intervals established at block 508 prior to ATP onset, and the predicted TWA phase, may continue to be used to complete the series of ATP pulses at alternating ATP time intervals. A comparison between the T-wave time intervals following ATP pulses determined at blocks 604 and 608 and the R-T time intervals determined prior to ATP for determining if the TWA has changed may account for an expected difference between the intrinsic R-T time interval and the pacing pulse-to-T-wave time interval.

If the TWA detected prior to the leading ATP pulse is still present but is altered by the initiation of ATP, the next ATP interval may be adjusted at block 612 based on the T-wave intervals determined after ATP pulses. The process may return to block 606 to deliver the next ATP pulse at the adjusted ATP interval. The process of sensing the T-wave following a delivered ATP pulse and determining if TWA is still present or altered at block 610 may be repeated pulse by pulse during ATP delivery until all pulses of the ATP series are delivered. In other examples, determining if TWA is still present or altered after the onset of ATP therapy may be performed by sensing only the first one, two, three, four or other predetermined number of T-waves during ATP delivery. In this way, monitoring of T-wave time intervals during ATP delivery may account for TWA that is started, terminated or altered by the delivery of ATP. If all ATP pulses of the scheduled series of pulses have been delivered, as determined at block 614, the control circuit 380 may return to block 502 to await the next tachyarrhythmia detection.

Figure 9:
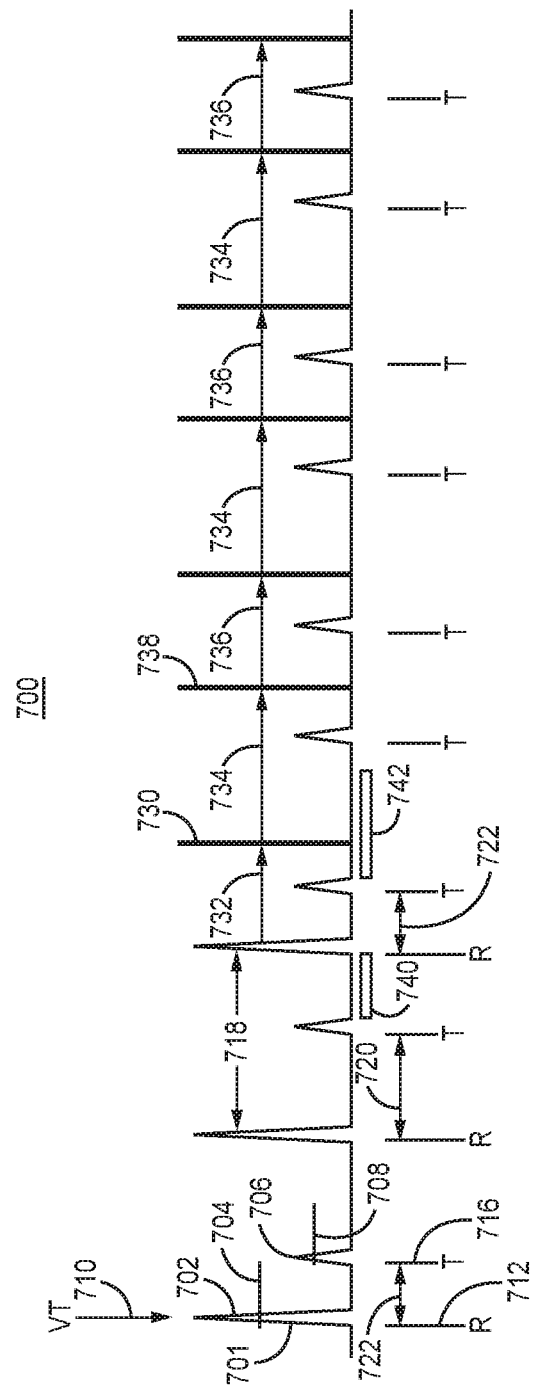
FIG. 9 is a timing diagram of ATP therapy delivered by a medical device according to one example of the techniques disclosed herein.

FIG. 9 is a timing diagram 700 of ATP therapy delivered by a medical device according to one example of the techniques disclosed herein. A conceptual diagram of a filtered and rectified cardiac electrical signal 701, produced by sensing circuit 386 from a cardiac electrical signal received from the patient's heart, includes intrinsic R-waves 702 and T-waves 706. Sensing circuit 386 may apply an R-wave sensing threshold 704 for sensing R-waves 702 and a T-wave sensing threshold 708 for sensing T-waves 706. Various methods may be used for sensing R-waves 702 and T-waves 706 using one or more sensing channels as described above. Such methods may include comparing one or more features of the cardiac signal 701 (such as amplitude, width, area, timing relative to a sensed R-wave, etc.) to T-wave sensing criteria and/or performing cardiac signal waveform morphology analysis for detecting a waveform morphology that matches an expected T-wave morphology. Examples of methods that may be used for sensing T-waves and detecting TWA are generally disclosed in U.S. Publication No. 2006/0116596 (Zhou, et al.), incorporated herein by reference in its entirety. Sensing circuit 386 may produce an R-wave sensed event signal 712 in response to sensing an R-wave 702 and a T-wave sensed event signal 716 in response to sensing a T-wave 706.

Control circuit 380 receives the R-wave sensed event signals 712 and the T-wave sensed event signals 716. R-wave sensed event signals 712 are used for determining RR intervals and detecting VT or VF. In the example shown, a VT detection 710 is made by control circuit 380. Prior to and/or after VT detection 710, control circuit 380 may determine R-T intervals 720 and 722 between a pair of consecutively received R-wave sensed event and T-wave sensed event signals 712 and 716. Control circuit 380 may be configured to detect TWA based on alternating R-T intervals 720 and 722, where every other R-T interval 722 is shorter (or longer) than the intervening R-T interval 720. Based on the alternating R-T intervals 720 and 722, control circuit 380 may establish two different ATP intervals 734 and 736 that are both shorter than the VT cycle length 718 but different from each other.

After the VT detection 710, control circuit 380 may determine a subsequent R-T interval 720 or 722 to predict the phase of the TWA in the next cardiac cycle during which a leading ATP pulse 730 is delivered. In some instances, if the current R-T interval 722 immediately following VT detection 710 is the short phase, the next R-T interval 720 is predicted to be the long phase, which may be associated with a relatively late, short excitable gap 740. Control circuit 380 may control therapy delivery circuit 384 to withhold ATP for one cardiac cycle corresponding to the long phase of the TWA (long R-T interval 720) and deliver the leading ATP pulse 730 at a coupling interval 732 during a cardiac cycle corresponding to the short phase of the TWA (short R-T interval 722), when the excitable gap 742 is expected to start earlier and be relatively longer. In other examples, the leading ATP pulse may be synchronized to the next sensed R-wave following VT detection 710, independent of TWA phase.

The coupling interval 732 may be set based on the VT cycle length 718, and may be the same as one of the established ATP intervals 734 and 736 or different than both ATP intervals 734 and 736. In some examples, the coupling interval 732 is set to the ATP interval 734 or 736 corresponding to the expected phase of the TWA of the cardiac cycle during which the leading pulse 730 is being delivered. In the example shown, control circuit 380 detects a short RT interval 722 immediately following VT detection 710, waits one cardiac cycle corresponding to the long RT interval 720 (and shortened excitable gap 740) to deliver the leading ATP pulse 730 at a coupling interval 732, which may be set to the short ATP interval 736 corresponding to the short TWA phase (short RT interval 722) expected after the long RT interval 720 and corresponding to a relatively earlier and longer excitable gap 742. Each ATP pulse 738 following the leading pulse 730 is delivered at an alternating ATP time interval 734 or 736 following the immediately preceding ATP pulse. Each pair of consecutive ATP pulses is separated by one of the alternating ATP time intervals 732 or 734.

In some examples, the alternating ATP time intervals 734 and 736 are pre-determined, based on TWA detection prior to the leading ATP pulse 730. In other examples, e.g., using the methods of FIG. 6 or FIG. 8, the alternating ATP time intervals 734 and 736 between pairs of consecutive ATP pulses may occur by sensing T-waves 706 during ATP delivery and delivering ATP pulses 738 based on T-wave timing (e.g., a fixed interval after a T-wave sensed event signal) or based on T-wave time intervals (e.g., a fixed percentage or interval greater than the interval from an ATP pulse to a T-wave sensed event signal) determined during ATP delivery. In this way, each ATP pulse 738 has a high likelihood of being delivered relatively early during the excitable gap 740 or 742 even in the presence of TWA, increasing the likelihood of terminating the detected ventricular tachyarrhythmia.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single device, circuit or unit for purposes of clarity, it should be understood that the techniques of this disclosure may be performed by a combination of units or circuits associated with, for example, one or more medical devices.

In one or more examples, the functions described may be implemented in hardware, software, firmware, or any combination thereof. If implemented in software, the functions may be stored as one or more instructions or code on a non-transitory computer-readable medium and executed by a hardware-based processing unit. Computer-readable media may include non-transitory computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an IMD system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a sensing circuit configured to receive a cardiac electrical signal from a patient's heart and sense R-waves and T-waves from the cardiac electrical signal;
a therapy delivery circuit configured to generate and deliver anti-tachycardia pacing (ATP) pulses to the patient's heart via electrodes coupled to the therapy delivery circuit;
a control circuit coupled to the sensing circuit and to the therapy delivery circuit and configured to:
detect a ventricular tachyarrhythmia from the cardiac electrical signal received by the sensing circuit;
responsive to the detected ventricular tachyarrhythmia, control the therapy delivery circuit to:
deliver a plurality of ATP pulses at alternating ATP time intervals comprising at least a first ATP time interval separating a first pair of the plurality of the ATP pulses comprising a first ATP pulse and a second ATP pulse consecutively following the first ATP pulse at the first ATP time interval, a second ATP time interval separating a second pair of the plurality of ATP pulses comprising the second ATP pulse and a third ATP pulse consecutively following the second ATP pulse at the second ATP time interval, the second ATP time interval being different than the first ATP time interval and consecutively following the first ATP time interval, and a fourth ATP pulse consecutively following the third ATP pulse at the first ATP time interval.

2. The device of claim 1, wherein the control circuit is further configured to:
set the first ATP time interval based on a time of a first one of the T-waves that is sensed by the sensing circuit; and
control the therapy delivery circuit to deliver a second pulse of the first pair at the first ATP time interval following a first pulse of the first pair.

3. The device of claim 2, wherein the control circuit is further configured to set the first ATP time interval based on a time of the first one of the T-waves sensed by the sensing circuit that is consecutive with a leading pulse of the plurality of ATP pulses.

4. The device of claim 2, wherein:
the sensing circuit is configured to sense the first one of the T-waves prior to the first pulse; and
the control circuit is configured to:
detect T-wave alternans from the cardiac electrical signal received by the sensing circuit prior to delivering the plurality of ATP pulses;
determine a phase of the T-wave alternans in response to sensing the first one of the T-waves; and
set the first ATP time interval based on the determined phase.

5. The device of claim 4, wherein the control circuit is further configured to:
determine a first R-T time interval of a first phase of the detected T-wave alternans;
determine a second R-T time interval of a second phase of the detected T-wave alternans; and
establish the first ATP time interval and the second ATP time interval based on the first and second R-T time intervals.

6. The device of claim 2, wherein the second pair of pulses comprises the second pulse of the first pair and a third pulse of the plurality of ATP pulses, wherein:
the sensing circuit is configured to sense a second one of the T-waves consecutive with the second pulse; and
the control circuit is further configured to:
set the second ATP time interval based on a time of the second one of the T-waves; and
deliver the third pulse at the second ATP time interval following the second pulse of the first pair.

7. The device of claim 1, wherein the control circuit is further configured to:
determine a cycle length of the ventricular tachyarrhythmia;
set a base ATP interval based on the cycle length;
adjust the base ATP interval to one of the first ATP time interval and the second ATP time interval in response to a timing of a first one of the T-waves sensed by the sensing circuit.

8. The device of claim 6, wherein adjusting the base ATP interval comprises:
determining a T-wave time interval ending with the first one of the T-waves and starting with a first one of the R-waves sensed by the sensing circuit or a delivered one of the plurality of ATP pulses; and
adjusting the base ATP interval to an interval longer than the T-wave time interval and shorter than the ventricular cycle length.

9. The device of claim 1, wherein the control circuit is further configured to:
determine a cycle length of the ventricular tachyarrhythmia;
set a coupling interval based on the cycle length; and
control the therapy delivery circuit to:
deliver a leading one of the plurality of ATP pulses at the coupling interval following a first one of the R-waves sensed by the sensing circuit; and
deliver a second ATP pulse following the leading ATP pulse at the first ATP time interval, different than the coupling interval.

10. The device of claim 9, wherein the control circuit is further configured to control the therapy delivery circuit to deliver a third ATP pulse following the second ATP pulse at the second ATP time interval, wherein the second ATP time interval equals the coupling interval.

11. The device of claim 1, wherein the control circuit is further configured to:
detect T-wave alternans from the cardiac electrical signal received by the sensing circuit prior to delivering the plurality of anti-tachycardia pacing pulses;
determine a phase of the T-wave alternans in response to at least one of the T-waves sensed by the sensing circuit;
wait for a first one of the R-waves sensed by the sensing circuit that leads a short phase of the T-wave alternans; and
deliver a leading one of the plurality of ATP pulses after a coupling interval following the first one of the R-waves leading the short phase of the T-wave alternans.

12. A method comprising:
  detecting a ventricular tachyarrhythmia from a cardiac electrical signal device of a patient's heart;
  responsive to detecting the ventricular tachyarrhythmia, delivering a plurality of anti-tachycardia pacing (ATP) pulses at alternating ATP time intervals comprising at least a first ATP time interval separating a first pair of the plurality of the ATP pulses comprising a first ATP pulse and a second ATP pulse consecutively following the first ATP pulse at the first ATP time interval, a second ATP time interval separating a second pair of the plurality of ATP pulses comprising the second ATP pulse and a third ATP pulse consecutively following the second ATP pulse at the second ATP time interval, the second ATP time interval being different than the first ATP time interval and consecutively following the first ATP time interval, and a fourth ATP pulse consecutively following the third ATP pulse at the first ATP time interval.

13. The method of claim 12, further comprising:
  setting the first ATP time interval based on a time of a first one of the sensed T-waves; and
  delivering a second pulse of the first pair at the first ATP time interval following a first pulse of the first pair.

14. The method of claim 13, further comprising setting the first ATP time interval based on a time of the first one of the T-waves consecutive with a leading pulse of the plurality of ATP pulses.

15. The method of claim 13, further comprising:
  sensing the first one of the T-waves prior to the first pulse;
  detecting T-wave alternans from the cardiac electrical signal prior to delivering the plurality of ATP pulses;
  determining a phase of the T-wave alternans in response to sensing the first one of the T-waves prior to the first pulse; and
  setting the first ATP time interval based on the determined phase.

16. The method of claim 15, further comprising:
  determining a first R-T time interval of a first phase of the detected T-wave alternans;
  determining a second R-T time interval of a second phase of the detected T-wave alternans; and
  establishing the first ATP time interval and the second ATP time interval based on the first and second R-T time intervals.

17. The method of claim 13, wherein the second pair of pulses comprises the second pulse of the first pair and a third pulse of the plurality of ATP pulses, the method further comprising:
  sensing a second one of the sensed T-waves consecutive with the second pulse; setting the second ATP time interval based on a time of the second one of the sensed T-waves; and
  delivering the third pulse at the second ATP time interval following the second pulse of the first pair.

18. The method of claim 12, further comprising:
  determining a cycle length of the ventricular tachyarrhythmia;
  setting a base ATP interval based on the cycle length;
  adjusting the base ATP interval to one of the first ATP time interval and the second ATP time interval in response to a timing of a first one of the sensed T-waves.

19. The method of claim 18, wherein adjusting the base ATP interval comprises:
  determining a T-wave time interval ending with the first one of the sensed T-waves and starting with a first one of the sensed R-waves or a delivered one of the plurality of ATP pulses; and
  adjusting the base ATP interval to an interval longer than the T-wave time interval and shorter than the ventricular cycle length.

20. The method of claim 12, further comprising:
  determining a cycle length of the ventricular tachyarrhythmia;
  setting a coupling interval based on the cycle length;
  delivering a leading one of the plurality of ATP pulses at the coupling interval following a first one of the sensed R-waves; and
  delivering a second ATP pulse following the leading ATP pulse at the first ATP time interval, different than the coupling interval.

21. The method of claim 18, further comprising delivering a third ATP pulse following the second ATP pulse at the second ATP time interval, wherein the second ATP time interval equals the coupling interval.

22. The method of claim 12, further comprising:
  detecting T-wave alternans from the cardiac electrical signal prior to delivering the plurality of anti-tachycardia pacing pulses;
  determining a phase of the T-wave alternans in response to at least one of the sensed T-waves;
  waiting for a first one of the sensed R-waves that leads a short phase of the T-wave alternans; and
  delivering a leading one of the plurality of ATP pulses after a coupling interval following the first one of the sensed R-waves leading the short phase of the T-wave alternans.

23. A non-transitory computer-readable medium storing a set of instructions which when executed by a control circuit of a medical device, cause the medical device to:
  detect a ventricular tachyarrhythmia from a cardiac electrical signal;
  responsive to the detected ventricular tachyarrhythmia, control a therapy delivery circuit of the medical device to deliver a plurality of anti-tachycardia pacing (ATP) pulses at alternating ATP time intervals comprising at least a first ATP time interval separating a first pair of the plurality of the ATP pulses comprising a first ATP pulse and a second ATP pulse consecutively following the first ATP pulse at the first ATP time interval, a second ATP time interval separating a second pair of the plurality of ATP pulses comprising the second ATP pulse and a third ATP pulse consecutively following the second ATP pulse at the second ATP time interval, the second ATP time interval being different than the first ATP time interval and consecutively following the first ATP time interval, and a fourth ATP pulse consecutively following the third ATP pulse at the first ATP time interval.

* * * * *